(12) United States Patent
Viola

(10) Patent No.: US 8,490,852 B2
(45) Date of Patent: *Jul. 23, 2013

(54) ENERGY STORED IN SPRING WITH CONTROLLED RELEASE

(75) Inventor: Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 514 days.

This patent is subject to a terminal disclaimer.

(21) Appl. No.: 12/729,358

(22) Filed: Mar. 23, 2010

(65) Prior Publication Data

US 2010/0170931 A1 Jul. 8, 2010

Related U.S. Application Data

(60) Continuation of application No. 12/172,287, filed on Jul. 14, 2008, now Pat. No. 8,336,752, which is a division of application No. 10/550,469, filed as application No. PCT/US2004/009442 on Mar. 26, 2004, now Pat. No. 7,559,449.

(60) Provisional application No. 60/458,086, filed on Mar. 26, 2003.

(51) Int. Cl.
*A61B 17/04* (2006.01)
*A61B 17/10* (2006.01)

(52) U.S. Cl.
USPC .................................................. 227/179.1

(58) Field of Classification Search
None
See application file for complete search history.

(56) References Cited

U.S. PATENT DOCUMENTS

| 2,060,814 | A | * | 11/1936 | Lewis | 173/41 |
| 2,574,875 | A | * | 11/1951 | Lang | 227/96 |
| 3,712,386 | A | * | 1/1973 | Peters | 173/46 |
| 3,948,259 | A | * | 4/1976 | Bolduc et al. | 128/831 |
| 4,215,808 | A | * | 8/1980 | Sollberger et al. | 227/146 |
| 4,329,121 | A | * | 5/1982 | Gregory | 417/270 |
| 4,522,207 | A | | 6/1985 | Klieman et al. | |
| 4,635,638 | A | * | 1/1987 | Weintraub et al. | 606/147 |
| 4,657,018 | A | * | 4/1987 | Hakky | 606/46 |
| 4,848,338 | A | * | 7/1989 | De Satnick et al. | 606/1 |
| 4,869,415 | A | | 9/1989 | Fox | |
| 4,943,294 | A | * | 7/1990 | Knapp | 606/117 |
| 4,951,861 | A | | 8/1990 | Schulze et al. | |
| 5,098,004 | A | | 3/1992 | Kerrigan | |
| 5,322,503 | A | * | 6/1994 | Desai | 604/21 |
| 5,350,390 | A | * | 9/1994 | Sher | 606/159 |
| 5,364,001 | A | | 11/1994 | Bryan | |

(Continued)

FOREIGN PATENT DOCUMENTS

FR 2701832 9/1994

OTHER PUBLICATIONS

PCT International Search Report for PCT/US2004/009442 date of completion is Sep. 7, 2004 (3 pages).

*Primary Examiner* — Robert Long

(57) ABSTRACT

There is provided a surgical instrument including a handle having an elongated tubular member extending distally from the handle and one or more end effectors mounted on the distal end of the elongate tubular member. A driver is movably mounted within the handle and elongate tubular member in order to operate the end effectors. The surgical instrument includes an energy storage mechanism for storing and providing energy to move the driver and thereby actuate the surgical instrument. Various actuation mechanisms are disclosed which are operable on the energy storage mechanism to control the rate of release of the energy stored in the energy storage mechanism.

15 Claims, 5 Drawing Sheets

U.S. PATENT DOCUMENTS

| | | | |
|---|---|---|---|
| 5,411,508 A * | 5/1995 | Bessler et al. | 606/153 |
| 5,425,164 A * | 6/1995 | El Dessouky | 29/243.524 |
| 5,591,184 A * | 1/1997 | McDonnell et al. | 606/167 |
| 5,601,601 A | 2/1997 | Christian et al. | |
| 5,645,209 A | 7/1997 | Green et al. | |
| 5,716,366 A | 2/1998 | Yates | |
| 5,720,423 A * | 2/1998 | Kondo et al. | 227/130 |
| 5,918,370 A * | 7/1999 | Wells | 30/228 |
| 6,443,973 B1 | 9/2002 | Whitman | |
| 6,457,625 B1 | 10/2002 | Tormala et al. | |
| 6,644,532 B2 * | 11/2003 | Green et al. | 227/176.1 |
| 8,333,773 B2 * | 12/2012 | DiMauro et al. | 606/93 |
| 2006/0231811 A1 * | 10/2006 | Koenecke | 254/228 |
| 2007/0027230 A1 * | 2/2007 | Beyar et al. | 523/117 |
| 2007/0123850 A1 * | 5/2007 | Cucin | 606/45 |
| 2009/0076486 A1 * | 3/2009 | Cucin | 604/542 |
| 2011/0282382 A1 * | 11/2011 | McAlister et al. | 606/213 |

* cited by examiner

ENERGY STORED IN SPRING WITH CONTROLLED RELEASE

CROSS REFERENCE TO RELATED APPLICATION

This application is a continuation of U.S. application Ser. No. 12/172,287 filed Jul. 14, 2008, which is a divisional of U.S. application Ser. No. 10/550,469 filed Sep. 22, 2005, which claims the benefit of U.S. Provisional Application Ser. No. 60/458,086, filed Mar. 26, 2003, the entire disclosure of which is incorporated by reference herein, in their entirety.

BACKGROUND

In certain devices, such as surgical instruments, it is desirable to store energy within the instrument to facilitate firing the instrument. One such device is a clip applier disclosed in U.S. Pat. No. 4,611,595. This clip applier stores energy in a spring which is retained by a latch mechanism. Movement of a handle disengages the latch resulting in rapid and uncontrolled release of the stored energy to actuate the clip applier. However, in some instruments it would be desirable to have structure for allowing for a controlled release of the stored energy to control the rate of actuation of the instrument.

Further, many surgical instruments, such as 60 mm staplers used in thick tissue, require more energy than can be comfortably developed by a single squeeze of a human hand. Currently, surgeons may use two hands to fire, or use instruments which require multiple, lower effort squeezes, to fire. Thus, it would also be desirable to have a surgical instrument that can be pre-energized by pumping at least once and possibly several times to store potential energy in a spring. This pre-energizing may be done by a surgical nurse or other assistant. This is particularly important during long procedures where fatigue, from multiple firings, may be uncomfortable to the surgeon.

SUMMARY

There is provided a surgical instrument for use in actuating various end effectors. The surgical instrument generally includes a handle having an elongated tubular member extending distally from the handle. The various end effectors may be provided on the distal end of the elongate tubular member and actuated by a driver, such as, for example, a drive rod, which is mounted for movement relative to the elongate member. The surgical instrument also includes an energy storing mechanism for storing and providing energy to move the drive rod and thus actuate the end effectors. Various embodiments of actuation mechanisms are disclosed which are operable on the energy storage mechanism to restrain, and control the rate of, release of the energy stored in the energy storage mechanism.

The energy storage mechanism generally includes a cylinder having a spring biased piston positioned therein. A piston rod is attached to the piston and extends through the cylinder to engage gear structure associated with the drive rod. The handle is provided at a second end of the piston rod to compress the spring and piston within the cylinder. Release of the energy stored in the spring forces the piston rod to move in a direction which actuates the gear structure to drive the drive rod and thus actuate the end effectors.

In a first embodiment, a fluid system is associated with the cylinder and piston to restrain and dampen the movement of the piston. A transfer system is provided to transfer the fluid from one side of the piston to the other side of the piston within the cylinder. The transfer system may additionally include a bypass mechanism allowing the surgeon to compress the spring and piston and thus transfer the fluid within the cylinder.

An actuation system of an alternative embodiment utilizes a brake mechanism operable on the gear structure connecting the piston rod to the drive rod. Depression of a trigger releases the pressure of the brake on the gear structure allowing the instrument to be fired.

Similarly, a further embodiment utilizes a similar brake mechanism to control the rate of release of the energy stored in the energy storage mechanism. This embodiment utilizes a particularly useful linkage to provide a mechanical advantage and thus greater pressure on the gear mechanism in situations where the spring is of a particularly high strength.

There are also disclosed additional embodiments of the surgical instrument which utilize a flywheel to provide a dampening effect on the gear mechanism as the gear mechanism is driven by the piston rod. In one embodiment, an idler gear wheel is attached to the flywheel and a cam surface is provided on a trigger to frictionally engage the flywheel and thus control the rate of release of energy stored in the spring. In an alternative embodiment, a multi-gear structure is associated with the flywheel to provide greater mechanical advantages as disclosed herein.

DESCRIPTION OF THE DRAWINGS

Various embodiments are disclosed herein with reference to the drawings wherein.

DETAILED DESCRIPTION

There are disclosed various embodiments of a handle assembly in which energy is stored in a spring from one or more manual input actions and restrained by various actuation structure. When the surgeon actuates a trigger the spring is unrestrained at controllable rates thereby allowing the stored energy in the spring to be delivered into the working mechanism to perform the desired function.

In general, a damping means is incorporated into the system, to control the rate of energy release to a smooth, deliberate action. The damping may be hydraulic, pneumatic, mechanical or other suitable means. If desired, the release may be made controllable by the surgeon through the use of a valve, brake, flywheel or other suitable control means, so as to allow him or her to go faster, slower, or even pause the release action.

Figure 1:
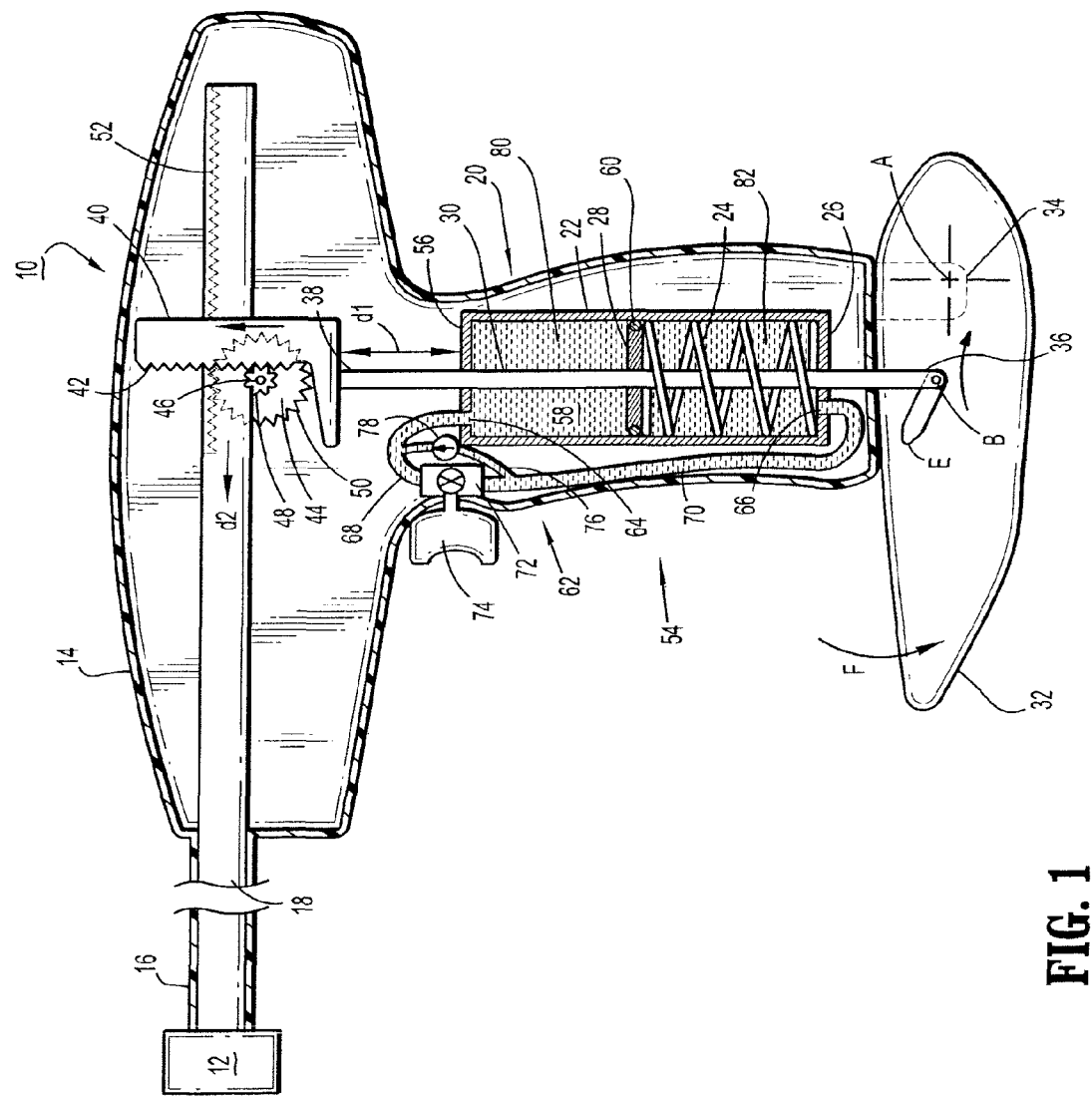
FIG. 1 is a schematic view of an energy storage system, in an actuator handle, employing a hydraulic dampening structure.

Referring to FIG. 1, an instrument 10 is disclosed for actuating various end effectors 12. Instrument 10 generally includes a handle body 14, an elongate tubular member 16 extending distally from handle body 14 and a driver, such as, a drive rod 18 longitudinally movable therein to actuate end effector 12. While elongate tubular member 16 is illustrated as being fixed to handle body 14, elongate tubular member 16 may alternatively be mounted for rotation with respect to handle body 14.

An energy storage system 20 is provided to store energy and provide it to drive rod 18 upon release. Energy storage system 20 generally includes a cylinder 22 having a compressible spring 24, such as, for example, a die spring, mounted therein. Spring 24 is positioned between a bottom cap 26 of cylinder 22 and a piston 28 slidably mounted in the cylinder 22. A piston rod 30 extends through cylinder 22 and is affixed to the piston 28. An energizing handle 32 is mounted at a pivot point A to a bracket 34 on the handle body 14. A lower end 36 of the piston rod 30 is pivotally mounted to the energizing handle 32 at a pivot point B and rides in slot E of energizing handle 32. An upper end 38 of the piston rod 30 is connected to an L-rack 40 having L-rack teeth 42. A large gear wheel 44 and a small gear wheel 46 are affixed to each other and are rotatably mounted to the handle body 14. Teeth 48 on the small gear wheel 46 engage L-teeth 42 on the L-rack 40 while teeth 50 on the large gear wheel 44 engage drive teeth 52 on the drive rod 18. Configuration of the gear ratios are such that a distance movement d1 of piston rod 30 results in a distance movement d2 of the drive rod 18. In one useful embodiment, a movement d1=1 inch results in a distance movement d2=approximately 2.6 inches.

By rotating energizing handle 32 about pivot A, in the direction of arrow F, piston rod 30 is pulled down compressing spring 24 between piston 28 and bottom cap 26. Pulling piston rod 30 down pulls L-rack 40 down causing L-rack teeth 42 to rotate large and small gear wheels 44 and 46 clockwise by engagement with teeth 48 on small gear wheel 46. As large gear wheel 44 rotates clockwise, teeth 50 draw drive rod 18 proximally by engagement with drive teeth 52. This motion draws drive rod 18 to a proximal position.

As noted above, various embodiments of an actuation mechanism are provided to restrain compressed spring 24 and allow for controlled release of the energy stored therein. With continued reference to FIG. 1, a first embodiment of an actuation mechanism having a hydraulic system 54 is provided to control the release of spring 24 and provide greater control of the actuation of the instrument end effectors 12. Cylinder 22 is sealed by a top cap 56 and bottom cap 26 and is provided with an incompressible hydraulic fluid 58 on either side of piston 28. In one embodiment, piston 28 is provided with an 0-ring 60 to isolate fluid 58 on either side of piston 28 and allow smooth movement of piston 28 within cylinder 22.

A transfer system 62 is provided between an upper port 64 and a lower port 66 in top and bottom caps 56,26 to move hydraulic fluid 58 from one side of piston 28 to the other within cylinder 22 as die spring 24 is compressed. Transfer system 62 includes upper and lower tubes 68,70 which are in fluid communication with the upper and lower ports 64,66. Movement of piston 28 within cylinder 22 forces hydraulic fluid 58 from one side of piston 28 to the other via upper and lower tubes 68,70.

The actuation system also includes a valve 72 positioned between upper and lower tubes 68,70, respectively, and a valve trigger 74 to actuate valve 72. Depression of valve trigger 74 progressively opens valve 72 to allow for flow of hydraulic fluid 58. When valve trigger 74 is not depressed valve 72 is closed and no fluid 58 can flow therethrough.

In order to allow for movement of fluid 58 from one side of piston 28 to the other during compression of spring 24, there is provided a bypass system 76 having a one way check valve 78 positioned around valve 72 and between the upper and lower tubes 68,70, respectively. One way check valve 78 acts as a latch or restraining mechanism which will only allow for flow of fluid 58 in the direction from the lower tube 70 to the upper tube 68 during compression of spring 24.

In operation, energizing handle 32 is actuated to compress spring 24 and draw drive rod 18 proximally as described hereinabove. Valve 72 is closed and check valve 78 allows fluid to flow from lower tube 70 to upper tube 68. Once spring 24 is fully compressed, the pressure of fluid 58 in an upper chamber 80 of cylinder 22 maintains spring 24 in compression. Fluid 58 cannot flow back through bypass system 76 and valve 72 is closed. To controllably release spring 24 pressure and thus actuate the instrument, valve trigger 74 is depressed to allow fluid 58 to flow from upper tube 68 to lower tube 70 and lessen the fluid pressure in the upper chamber 80 as the fluid is transferred to a lower chamber 82. Upon release of spring 24, piston rod 30 moves up rotating large and small gear wheels 44 and 46 in a counter clockwise rotation and propelling drive rod 18 distally to actuate the end effector 12. The release of pressure and thus actuation of the instrument can be precisely controlled by the operator. By manipulating valve trigger 74, actuation can be instant and rapid, slow and progressive or even intermittent by repeated small depression of valve trigger 74.

A further function of hydraulic system 54 is to dampen the movement of piston 28 within cylinder 22 to provide a smooth and controlled release of spring 24 pressure and thus a very smooth actuation of the instrument.

Figure 2:
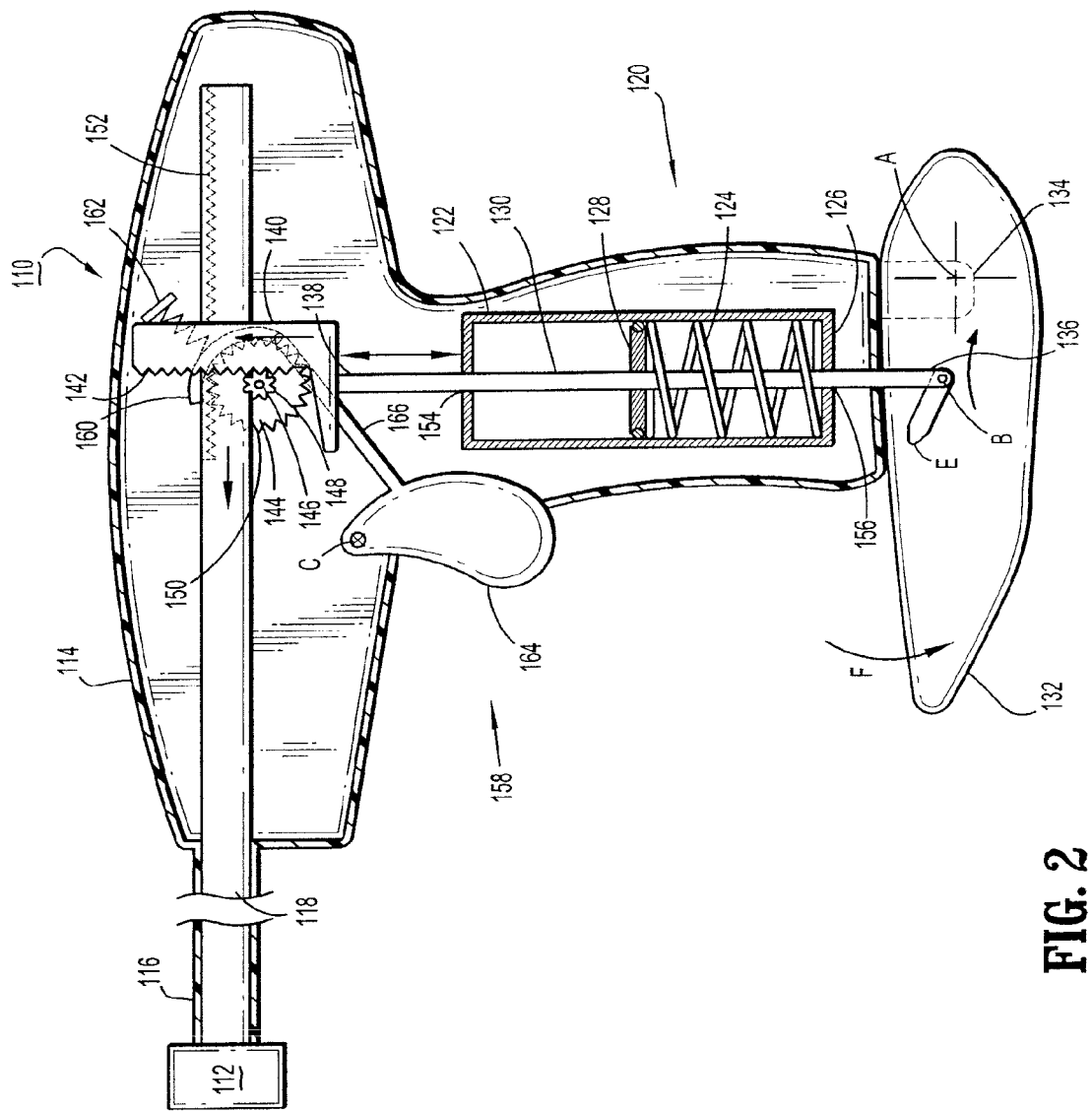
FIG. 2 is a schematic view of an energy storage system, in a handle mechanism, employing a brake dampening system.

Referring now to FIG. 2, there is disclosed a second embodiment of a surgical instrument having an energy storage system. The second embodiment incorporates a brake system to controllably release the spring pressure. It should be noted that the common elements of the embodiment disclosed herein are substantially similar to the first embodiment. Instrument 110 is designed to provide actuation to associated end effectors 112.

Instrument 110 generally includes a handle body 114 having an elongated tubular member 116 extending distally therefrom. A drive rod 118 is movably mounted in handle body 114 and elongated tubular member 116 and is powered by an energy storage system 120 in the manner described above with respect to energy storage system 20. Energy storage system 120 includes a cylinder 122 having a spring 124, such as a die spring, positioned between a bottom cap 126 and a piston 128. A piston rod 130 is affixed to piston 128. An energizing handle 132 is pivotally mounted about point A to handle body 114 at bracket 134. A lower end 136 of piston rod 130 is affixed to energizing handle 132 and pivots at point B and rides in a slot E in energizing handle 132. Energy storage system 120 also includes upper piston rod end 138 attached to an L-rack 140 having L-rack teeth 142. Large and small gear wheels 144, 146 having gear teeth 150 and 148, respectively, function together with drive teeth 152 on drive rod 118 in the manner described above to power drive rod 118 in response to release of the energy stored in spring 124.

In the embodiment of FIG. 2, air fills cylinder 122 and upper and lower clearances 154,156 formed in cylinder 122 around piston rod 130 allows air to flow freely in and out of cylinder 122. In order to restrain spring 124 in the compressed state and allow for controlled release of spring 124 pressure and thus actuation of the instrument there is provided a brake system 158 which frictionally acts on large gear wheel 144. Brake system 158 includes a brake shoe 160 which frictionally engages large gear wheel 144. A bias spring 162 is provided to bias brake shoe 160 into engagement with large gear wheel 144 with sufficient force to prevent rotation of large gear wheel 144 and prevent release of compressed spring 124.

A trigger 164 is pivotally mounted to the housing at pivot C and connected to brake shoe 160 by a transfer bar 166. Depression of trigger 164 moves brake shoe 160 progressively out of engagement with large gear wheel 144 and against the bias of bias spring 162. This allows controlled release of the spring pressure in compressed spring 124 and thus controllable actuation of the instrument.

Figure 3:
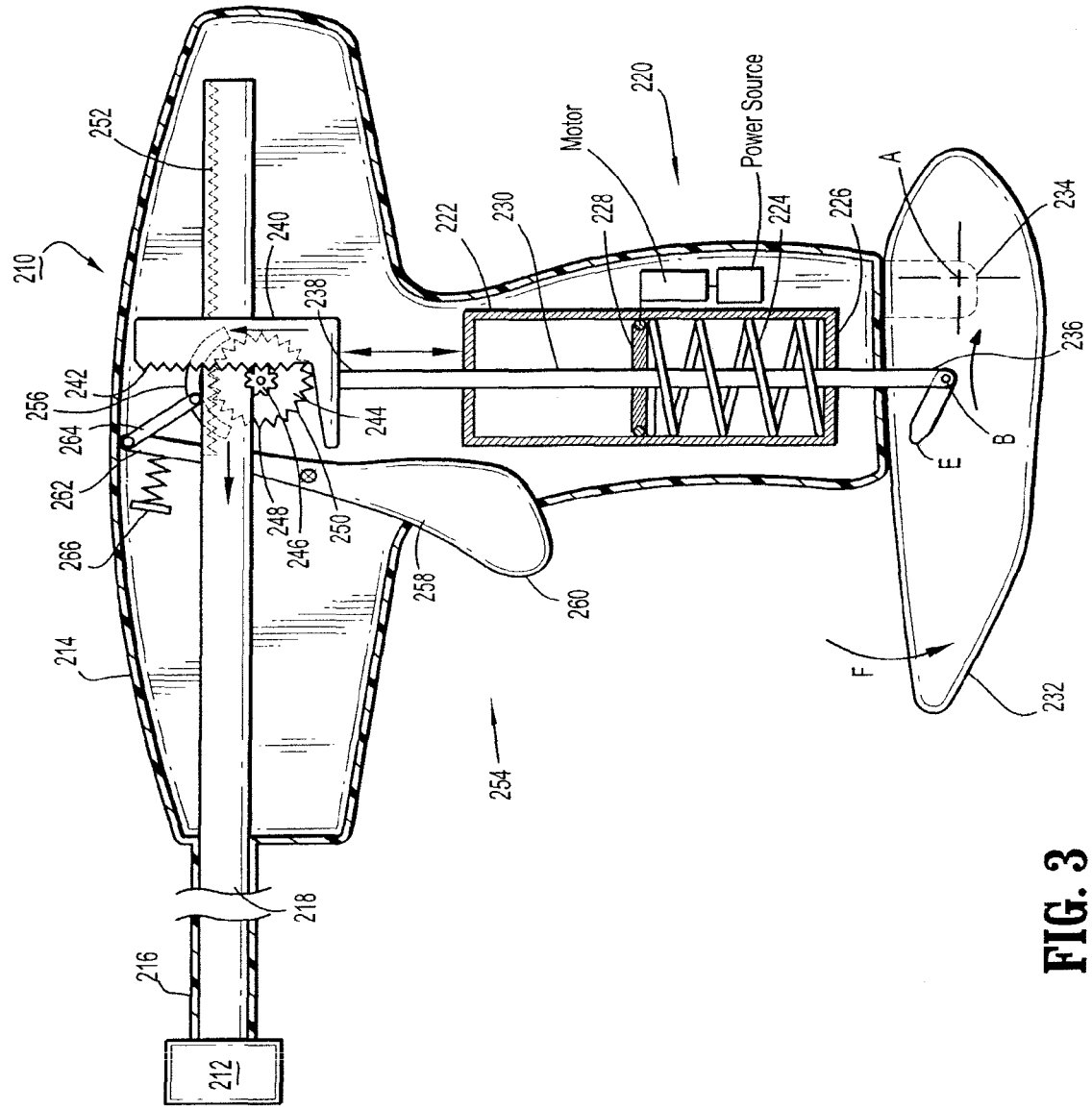
FIG. 3 is a schematic view of an energy storage system, in a handle mechanism, employing a second embodiment of a brake dampening system.

Referring now to FIG. 3, there is disclosed an alternate embodiment of a surgical instrument having another type of a brake assembly for controlled release of the die spring and actuation of the instrument. Instrument 210 generally includes a handle body 214 having an elongated tubular member 216 extending distally therefrom. A drive rod 218 is movably mounted in handle body 214 and elongated tubular member 216 and is powered by an energy storage system 220 in the manner described above with respect to energy storage system 20. Energy storage system 220 includes a cylinder 222 having a spring 224, such as a die spring, positioned between a bottom cap 226 and a piston 228. A piston rod 230 is affixed to piston 228. An energizing handle 232 is pivotally mounted about point A to handle body 214 at bracket 234. A lower end 236 of piston rod 230 is affixed to energizing handle 232 and pivots at point B and rides in slot E in energizing handle 232. Energy storage system 220 also includes upper piston rod end 238 attached to an L-rack 240 having L-rack teeth 242. Large and small gear wheels 244,246 having gear teeth 250 and 248, respectively, function together with drive teeth 252 on drive rod 218 in the manner described above to power drive rod 218 in response to release of the energy stored in spring 224.

As noted above, an actuation system is provided to control the rate of release of spring 224. An actuation or brake assembly 254 is provided similar to that of FIG. 2. Brake assembly 254 includes a brake 256 which is provided to pivotally engage large gear wheel 244 to control motion thereof. A trigger 258 is pivotally mounted to handle body 214 at a fixed, generally central point. Trigger 258 is relatively long to provide additional leverage and reduce the pressure on trigger 258 needed to actuate the instrument. A first end 260 of trigger 258 extends out of handle body 214 and a second end 262 is connected to brake 256 by a linkage 264. A biasing spring 266 provided in handle body 214 acts on second end 262 to bias brake 256 into engagement with large gear wheel 244.

In a manner similar to that of the embodiment in FIG. 2, depression of trigger 258 lifts brake 256 away from large gear wheel 244 to controllably release the energy stored in spring 224 and actuate the instrument.

Figure 4:
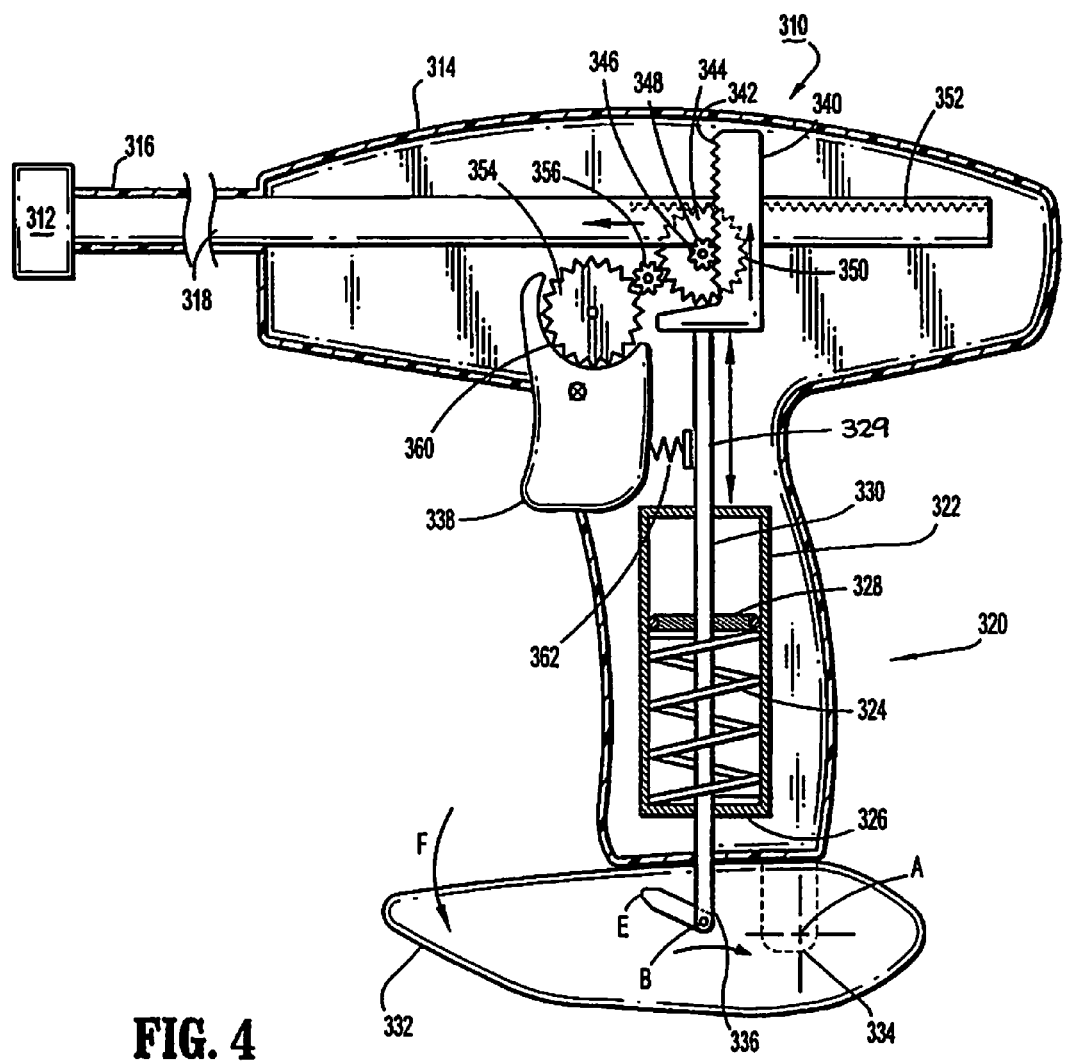
FIG. 4 is a schematic view of an energy storage system, in a handle mechanism, employing a flywheel dampening system.

Referring now to FIG. 4 there is disclosed an actuation system having a flywheel mechanism for controlled release of the energy stored in the spring and thus actuation of the instrument. Instrument 310, as with prior embodiments, is designed to provide actuation to associated instrument 310. Instrument 310 generally includes a handle body 314 having an elongated tubular member 316 extending distally therefrom. It should be noted that in all embodiments disclosed herein, elongated tubular member may be mounted for rotation on handle body 314. A drive rod 318 is movably mounted in handle body 314 and elongated tubular member 316 and is powered by an energy storage system 320. Energy storage system 320 includes a cylinder 322 having a spring 324, such as a die spring, positioned between a bottom cap 326 and a piston 328. A piston rod 330 is affixed to piston 328. An energizing handle 332 is pivotally mounted about point A to handle body 314 at bracket 334. A lower end 336 of piston rod 330 is pivotally mounted to energizing handle 332 and pivots at point B and rides in a slot E in energizing handle 232 as shown. Energy storage system 320 also includes upper piston rod end 329 attached to an L-rack 340 having L-rack teeth 342. Large and small gear wheels 344 and 346, having gear teeth 350 and 348, respectively, function together with drive teeth 352 on drive rod 318 in the matter described above. To power drive rod 318 in response to release of the energy stored in spring 324.

An alternative actuation system is provided to control the release of spring 324 by implementation of a fly wheel structure to smooth out actuation of instrument 310. A relatively large diameter flywheel 354 is rotatably mounted in the housing and connected to the large gear wheel 344 by a small diameter idler gear wheel 356. A trigger 338 is pivotally mounted to handle body 314 and includes a cam surface 360 engageable with flywheel 354. A trigger spring 362 biases trigger 338 such that cam surface 360 on trigger 338 firmly engages flywheel 354 to restrain the compressed spring 324. The difference in diameters of flywheel 354 and idler gear wheel 356 provides a mechanical advantage which reduces the pressure on trigger 338 needed to actuate the instrument.

Actuation of trigger 338 against the bias of trigger spring 362 brings cam surface 360 out of frictional engagement with flywheel 354. This allows for controlled release of the energy stored in spring 324 and controlled actuation of the surgical instrument 310. Importantly, the inertia present in flywheel 354 helps to retard startup rotation and thus actuation of the instrument 310. This retarded acceleration of the release of the spring pressure allows for smoother and slower actuation of drive rod 318.

Figure 5:
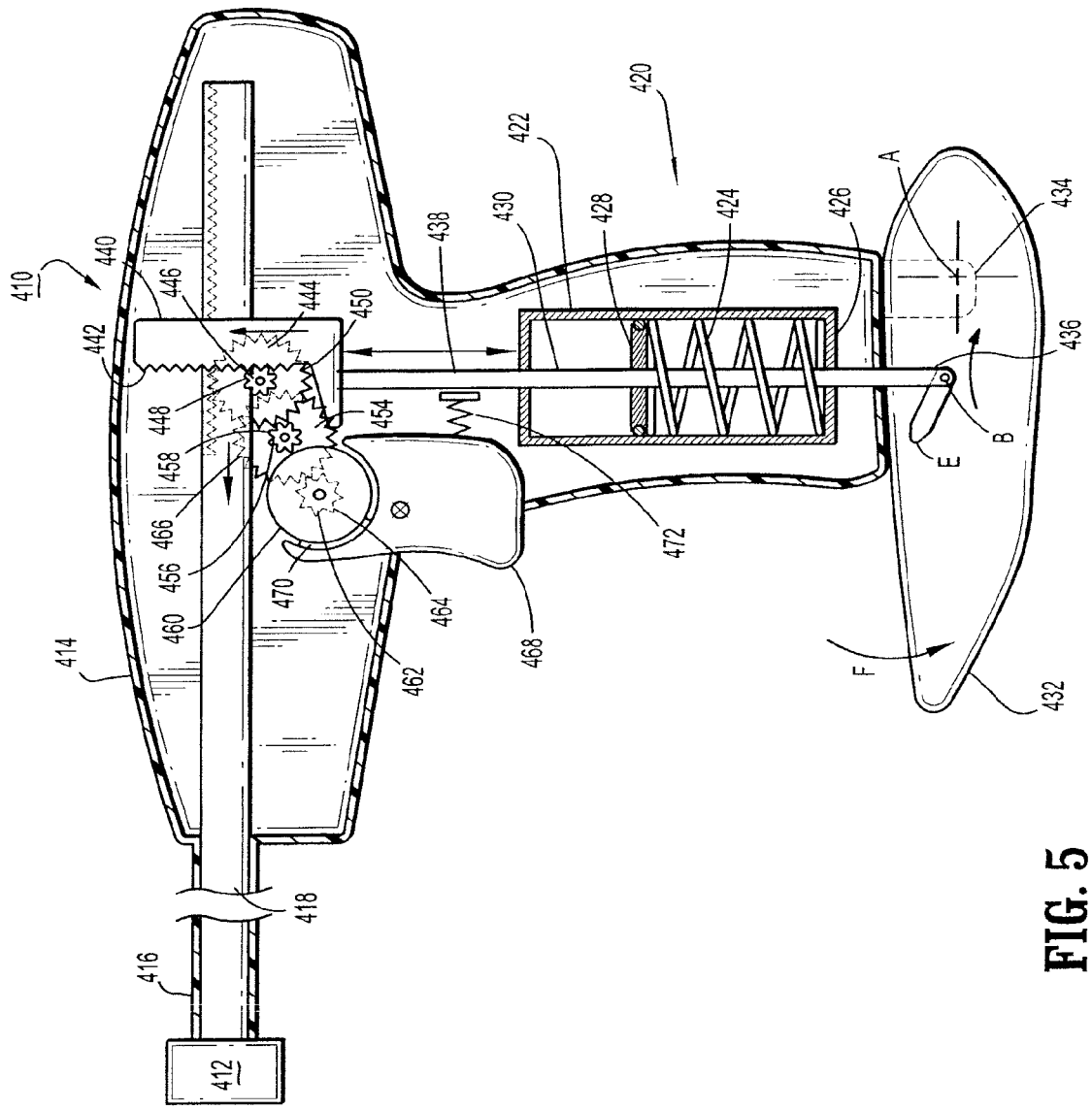
FIG. 5 is a schematic view of an energy storage system, in a handle mechanism, employing a multi-gear dampening system.

Referring now to FIG. 5, instrument 410, as with prior embodiments, is designed to provide actuation to associated instrument 410. Instrument 410 generally includes a handle body 414 having an elongated tubular member 416 extending distally therefrom. It should be noted that in all embodiments disclosed herein, elongated tubular member may be mounted for rotation on handle body 414. A drive rod 418 is movably mounted in handle body 414 and elongated tubular member 416 and is powered by an energy storage system 420. Energy storage system 420 includes a cylinder 422 having a spring 424, such as a die spring, positioned between a bottom cap 426 and a piston 428. A piston rod 430 is affixed to piston 428. An energizing handle 432 is pivotally mounted about point A to handle body 414 at bracket 434. A lower end 436 with piston rod 430 is affixed to energizing handle 432 and pivots at point B and rides in a slot E in energizing handle 432 as shown. Energy storage system 420 also includes upper piston rod end 428 attached to an L-rack 440 having L-rack teeth 442. Large and small gear wheels 444 and 446, having gear teeth 450 and 448, respectively, function together with drive teeth 452 on drive rod 418 in the manner described above, to power drive rod 418 in response to release of the energy stored in spring 424.

An alternative actuation system is provided to control the release of spring 424 by implementation of a multi-gear fly wheel structure to smooth out actuation of instrument 410.

An intermediate gear wheel 454 is affixed to idler gear wheel 456 such that idler gear wheel teeth 458 engage large gear wheel teeth 450. A flywheel 460 having a drive gear wheel 462 affixed thereto is rotatably mounted in handle body 414. Drive gear teeth 464 of drive gear wheel 462 are engageable with intermediate gear wheel teeth 466 of intermediate gear wheel 454 to rotate flywheel 460. A trigger 468 is pivotally mounted to handle body 414 and includes a braking mechanism similar to previous described embodiments including a cam surface 470 engageable with flywheel 460. The contact surfaces of cam surface 470 and flywheel 460 are relatively smooth to provide a smooth and progressive breaking action therebetween. A trigger spring 472 biases trigger 468 into engagement with flywheel 460. Operation is similar to the previous disclosed embodiments in that instrument 410 is energized by rotating energizing handle 432 to compress spring 424. A frictional engagement of cam surface 470 on trigger 468 against flywheel 460 prevents release of the energy. Once instrument 410 is to be actuated, trigger 468 is depressed lessening the engagement of cam surface 470 with flywheel 460. By varying the degree of pressure arm trigger 468 the amount of contact between cam surface 470 and flywheel 460 can be varied to thereby vary the rate of fire of instrument 410. Additionally, certain mechanical advantages are obtained through the use of multiple gear mechanisms. The multi-gear mechanisms allow a relatively large force to be applied to control the rate of release of energy stored in the spring in response to a relatively small force applied to the triggers. Additionally, the use of multiple gears having differing diameter allows a multiplication of force applied to the drive rod and thus the end effectors.

It is further envisioned that the input action to store energy may be motor driven, such that energy may commence being transferred into the spring during the period of time when a cartridge or disposable loading unit is being replaced, or even earlier, as right after the previous firing. Because the time period of transfer of energy from the motor to the spring is extended, a smaller, lighter motor and battery (or power supply) may be used.

It is additionally envisioned that, while the embodiments shown herein utilize a pistol style grip, other grip styles, such as, for example, straight, offset, etc. may also be used with the disclosed energy storage and actuation systems. Further, other cocking devices may be substituted for the pivoting energizing handle, such as, for example, a rotary cam, lead-screw compound lever, toggle, pull cable, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope of this disclosure.

What is claimed is:

1. A surgical instrument comprising:
    a handle having an elongate tubular member extending distally from the handle; an end effector provided on a distal end of the elongate tubular member;
    a driver mounted for movement relative to the elongate tubular member to operate the end effector;
    an energy storage mechanism for storing and providing energy to move the driver, the energy storage mechanism having a cylinder, a piston located within the cylinder to define a first chamber of the cylinder and a second chamber of the cylinder, the piston being in sealed relation with an inner wall of the cylinder, a fluid being located within the cylinder, the first and second chambers being connected to allow the fluid to pass between the first and second chambers;
    an actuation mechanism communicating with the energy storage mechanism to control the release of the energy stored in the energy storage mechanism, wherein the piston is operably associated with the driver to effect movement of the driver in a distal direction; and
    an energizing handle operatively attached with the piston for storing energy in the energy storage mechanism.

2. The surgical instrument as recited in claim 1, wherein the energy storage mechanism includes a spring positioned in one of the first and second chambers to engage the piston.

3. The surgical instrument as recited in claim 1, wherein the piston includes a piston rod and further comprising a gear structure supported on one end of the piston rod, the gear structure being operably coupled to the driver to effect movement of the driver in response to movement of the piston rod.

4. The surgical instrument as recited in claim 3, wherein the energizing handle is connected to the piston rod such that movement of the energizing handle compresses the spring.

5. The surgical instrument as recited in claim 1, wherein the actuation mechanism includes a first valve to control flow of the fluid between the first and second chambers.

6. The surgical instrument as recited in claim 5, wherein the actuation mechanism further includes a bypass valve to allow fluid flow from the second chamber to the first chamber when the first valve is closed.

7. The surgical instrument as recited in claim 4, wherein the driver defines a longitudinal axis which is orthogonal to the longitudinal axis of the piston rod.

8. The surgical instrument as recited in claim 1, wherein the energizing handle is pivotally attached to the handle.

9. The surgical instrument as recited in claim 5, further comprising a trigger being movable with respect to the handle, the trigger being operatively connected with the first valve.

10. A surgical instrument comprising:
    a handle having an elongate tubular member extending distally from the handle;
    an end effector provided on a distal end of the elongate tubular member;
    a driver mounted for movement relative to the elongate tubular member to operate the end effector, the driver defining a first longitudinal axis;
    an energy storage mechanism for storing and providing energy to effect movement of the driver, the energy storage mechanism having a piston and a piston rod, the piston being operably associated with the driver to effect movement of the driver in a distal direction, the piston rod defining a second longitudinal axis that is orthogonal to the first longitudinal axis;
    an actuation mechanism communicating with the energy storage mechanism to control the release of the energy stored in the energy storage mechanism; and
    a gear structure supported on one end of the piston rod, the gear structure being operably coupled to the driver to effect movement of the driver in response to movement of the piston rod.

11. A surgical instrument comprising:
    a handle having an elongate tubular member extending distally from the handle;
    an end effector provided on a distal end of the elongate tubular member;
    a driver mounted for movement relative to the elongate tubular member to operate the end effector, the driver defining a first longitudinal axis;
    an energy storage mechanism for storing and providing energy to effect movement of the driver, the energy storage mechanism having a piston and a piston rod, the piston being operably associated with the driver to effect movement of the driver in a distal direction, the piston rod defining a second longitudinal axis that is orthogonal to the first longitudinal axis; and
    an actuation mechanism communicating with the energy storage mechanism to control the release of the energy stored in the energy storage mechanism;
    wherein the actuation mechanism includes a fluid to control the release of energy stored in the energy storage mechanism and a first valve to control the flow of the fluid in a first direction and preventing flow of the fluid in a second direction.

12. The surgical instrument as recited in claim 11, wherein the actuation mechanism includes a bypass valve to allow movement of the fluid in the second direction when the first valve is closed, the bypass valve preventing movement of the fluid in the first direction.

13. A surgical instrument comprising:
   a handle having an elongate tubular member extending distally from the handle;
   an end effector provided on a distal end of the elongate tubular member;
   a driver mounted for movement relative to the elongate tubular member to operate the end effector, the driver defining a first longitudinal axis;
   an energy storage mechanism for storing and providing energy to effect movement of the driver, the energy storage mechanism having a piston and a piston rod, the piston being operably associated with the driver to effect movement of the driver in a distal direction, the piston rod defining a second longitudinal axis that is orthogonal to the first longitudinal axis; and
   an actuation mechanism communicating with the energy storage mechanism to control the release of the energy stored in the energy storage mechanism,
   wherein the actuation mechanism includes a fluid to control the release of energy stored in the energy storage mechanism, and
   wherein the actuation mechanism includes a brake system, the brake system being movable with respect to the energy storage mechanism, the brake system being operable on the energy storage mechanism to limit the release of energy stored in the energy storage mechanism.

14. A surgical instrument comprising:
   a handle having an elongate tubular member extending distally from the handle;
   an end effector provided on a distal end of the elongate tubular member;
   a driver mounted for movement relative to the elongate tubular member to operate the end effector, the driver defining a first longitudinal axis;
   an energy storage mechanism for storing and providing energy to effect movement of the driver, the energy storage mechanism having a piston and a piston rod, the piston being operably associated with the driver to effect movement of the driver in a distal direction, the piston rod defining a second longitudinal axis that is orthogonal to the first longitudinal axis; and
   an actuation mechanism communicating with the energy storage mechanism to control the release of the energy stored in the energy storage mechanism
   wherein the actuation mechanism includes a fluid to control the release of energy stored in the energy storage mechanism,
   wherein the actuation mechanism includes a flywheel operable on the energy storage mechanism.

15. The surgical instrument as recited in claim 10, wherein the actuation mechanism includes a brake operable on the gear structure.

* * * * *